US008263742B2

(12) United States Patent
Dunn

(10) Patent No.: US 8,263,742 B2
(45) Date of Patent: Sep. 11, 2012

(54) METHODS FOR DETECTION OF METHYL-CPG DINUCLEOTIDES

(75) Inventor: John J. Dunn, Bellport, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 13/085,219

(22) Filed: Apr. 12, 2011

(65) Prior Publication Data

US 2011/0245465 A1 Oct. 6, 2011

Related U.S. Application Data

(62) Division of application No. 12/507,522, filed on Jul. 22, 2009.

(51) Int. Cl.
*C07K 14/265* (2006.01)
(52) U.S. Cl. .......................... 530/358; 536/23.4; 435/7.1
(58) Field of Classification Search ........................ None
See application file for complete search history.

(56) References Cited

U.S. PATENT DOCUMENTS 4,943,636 A * 7/1990 Nitecki et al. ................ 546/294
6,331,393 B1 12/2001 Laird et al.

OTHER PUBLICATIONS

Tanaka, et al., "Direct Labeling of 5-Methylcytosine and its Applications," *J. Am. Chem. Soc.*, 129, 5612-5620 (2007).
Frommer, et al., "A Genomic Sequencing Protocol that Yields a Positive Display of 5-Methylcytosine Residues in Individual DNA Strands," *Proc. Natl. Acad. Sci. USA*, , 89, 1827-1831 (1992).
Clark, et al., "High Sensitivity Mapping of Methylated Cytosines," *Nucleic Acids Research*, 22, No. 15, 2990-2997 (1994).
Xiong, et al., "COBRA: A Sensitive and Quantitative DNA Methylation Assay," *Nucleic Acids Research*, 25, No. 12, 2532-2534 (1997).
Herman, et al., "Methylation-specific PCR: A Novel PCR Assay for Methylation Status of CpG Islands," *Proc. Natl. Acad. Sci. USA*, 93, 9821-9826 (1996).
Keshet, et al., "Evidence for an Instructive Mechanism of de novo Methylation in Cancer Cells," *Nature Genetics*, 38, No. 2, 149-153 (2006).
Weber, et al., "Chromosome-Wide and Promoter-Specific Analyses Identify Sites of Differential DNA Methylation in Normal and Transformed Human Cells," *Nature Genetics*, vol. 37, No. 8, 853-862 (2005).
Cross, et al., "Purification of CpG Islands Using a Methylated DNA Binding Column," *Nature Genetics*, 6, 236-244 (1994).
Gebhard, et al., "Genome-Wide Profiling of CpG Methylation Identifies Novel Targets of Aberrant Hypermethylation in Myeloid Leukemia," *Cancer Research*, 66, No. 12, 6118-6128 (2006).
Gebhard, et al., "Rapid and Sensitive Detection of CpG-methylation Using Methyl-binding (MB)-PCR," *Nucleic Acids Research*, 34, No. 11, e82-(2006).
MethylCollector (version B1), Catalog No. 55002, by Active Motif, Inc., Copyright 2007.
TransSignal™ Promoter Methylation Array, Catalog No. MA7010, by Panomics, Inc., Product User Manual, Revised Jul. 11, 2006.
EpiTect Bisulfite Handbook, 8-31, Apr. 2006.
Eads, et al., "MethyLight: A High-throughput Assay to Measure DNA Methylation," *Nucleic Acids Research*, 28, No. 8, e32, i-viii (2000).
Ho, et al., "MeCP2 Binding to DNA Depends upon Hydration at Methyl-CpG," *Molecular Cell*, 29, 525-531 (2008).
Rauch, et al., "MIRA-Assisted Microarray Analysis, a New Technology for the Determination of DNA Methylation Patterns, Identifies Frequent Methylation of Homeodomain-Containing Genes in Lung Cancer Cells," *Cancer Research*, 66, No. 16, 7939-7947 (2006).
Rauch, et al., "Methylated-CpG Island Recovery Assay: A New Technique for the Rapid Detection of Methylated-CpG Islands in Cancer," *Laboratory Investigation*, 1-9 (2005).
Schmidt, et al., "The Strep-tag System for One-step Purification and High-affinity Detection or Capturing of Proteins," *Nature Protocols*, 2, No. 6, 1528-1535 (2007).
Raleigh, et al., "McrA and McrB Restriction Phenotypes of Some *E. coli* Strains and Implications for Gene Cloning," *Nucleic Acids Research*, 16, No. 4, 1563-1575 (1988).
Raleigh, et al., "Genetics and Physical Mapping of the mcrA (rglA) and mcrB (rglB) Loci of *Escherichia coli* K12," *Genetics*, 122, 279-296 (1989).
Bujnicki, et al., "Atomic Model of the 5-methylcytosine-specific Restriction Enzyme McrA Reveals an Atypical Zinc Finger and Structural similarity to ββαMe Endonucleases," *Molecular Microbiology*, 37, No. 5, 1280-1281 (2000).
Hiom, et al., "Cloning and Structural Characterization of the mcrA Locus of *Escherichia coli*," *J. Of Bacteriology*, 173, No. 22, 7368-7373 (1991).
Ramalingam, et al., "Molecular Cloning and Sequencing of mcrA Locus and Identification of McrA Protein in *Escherichia coli*," *J. Biosci.*, 17 , No. 3, 217-232 (1992).
Fraga, et al., "The Affinity of Different MBD Proteins for a Specific Methylated Locus Depends on their Intrinsic Binding Properties," *Nucleic Acids Research*, 31, No. 6, 1765-1774 (2003).
Karimi, et al., "LUMA (LUminometric Methylation Assay)—A High Throughput Method to the Analysis of Genomic DNA Methylation," *Experimental Cell Research 312*, 1989-1995 (2006).
Gonzalgo, et al., Rapid Quantiation of Methylation Differences at Specific Sites Using Methylation-Sensitive Single Nucleotide Primer Extension (Ms-SNuPE), *Nucleic Acids Research*, 25, No. 12, 2529-2531 (1997).

* cited by examiner

*Primary Examiner* — Jim Ketter
(74) *Attorney, Agent, or Firm* — Dorene M. Price

(57) ABSTRACT

The invention provides methods for enriching methyl-CpG sequences from a DNA sample. The method makes use of conversion of cytosine residues to uracil under conditions in which methyl-cytosine residues are preserved. Additional methods of the invention enable to preservation of the context of me-CpG dinucleotides. The invention also provides a recombinant, full length and substantially pure McrA protein (rMcrA) for binding and isolation of DNA fragments containing the sequence 5'-$C^{Me}$CpGG-3'. Methods for making and using the rMcrA protein, and derivatives thereof are provided.

7 Claims, 7 Drawing Sheets

SEQUENCE LISTING

```
<160> NUMBER OF SEQ ID NOS: 20

<210> SEQ ID NO 1
<211> LENGTH: 34
<212> TYPE: DNA
<213> ORGANISM: Artificial Sequence
<220> FEATURE:
<223> OTHER INFORMATION: Adapter Cassette

<400> SEQUENCE: 1
agttattccg gactgtcgaa gctgaatgcc atgg                                   34

<210> SEQ ID NO 2
<211> LENGTH: 34
<212> TYPE: DNA
<213> ORGANISM: Artificial Sequence
<220> FEATURE:
<223> OTHER INFORMATION: Adapter Cassette

<400> SEQUENCE: 2
ccatggcatt cagcttcgac agtccggaat aact                                   34

<210> SEQ ID NO 3
<211> LENGTH: 36
<212> TYPE: DNA
<213> ORGANISM: Artificial Sequence
<220> FEATURE:
<223> OTHER INFORMATION: Adapter Cassette

<400> SEQUENCE: 3
taccatggca ttcagcttcg acagtccgga ataact                                 36

<210> SEQ ID NO 4
```

```
<211> LENGTH: 21
<212> TYPE: DNA
<213> ORGANISM: Artificial Sequence
<220> FEATURE:
<223> OTHER INFORMATION: ForwardPrimer

<400> SEQUENCE: 4
ttggattgtt gaagttgaat g                                            21

<210> SEQ ID NO 5
<211> LENGTH: 25
<212> TYPE: DNA
<213> ORGANISM: Artificial Sequence
<220> FEATURE:
<223> OTHER INFORMATION: ReversePrimer1

<400> SEQUENCE: 5
aaactatcaa aactaaatac cataa                                        25

<210> SEQ ID NO 6
<211> LENGTH: 27
<212> TYPE: DNA
<213> ORGANISM: Artificial Sequence
<220> FEATURE:
<223> OTHER INFORMATION: ReversePrimer1_1

<400> SEQUENCE: 6
aaactatcaa aactaaatac cataata                                      27

<210> SEQ ID NO 7
<211> LENGTH: 34
<212> TYPE: DNA
<213> ORGANISM: Artificial Sequence
<220> FEATURE:
<223> OTHER INFORMATION: AdapterCassette

<400> SEQUENCE: 7
agttattccg gactgtccgg aagctgaatg ccgg                              34

<210> SEQ ID NO 8
<211> LENGTH: 34
<212> TYPE: DNA
<213> ORGANISM: Artificial Sequence
<220> FEATURE:
<223> OTHER INFORMATION: AdapterCassette

<400> SEQUENCE: 8
ccggcattca gcttccggac agtccggaat aact                              34

<210> SEQ ID NO 9
<211> LENGTH: 36
<212> TYPE: DNA
<213> ORGANISM: Artificial Sequence
<220> FEATURE:
<223> OTHER INFORMATION: AdapterCassette

<400> SEQUENCE: 9
taccggcatt cagcttccgg acagtccgga ataact                            36

<210> SEQ ID NO 10
<211> LENGTH: 34
<212> TYPE: DNA
<213> ORGANISM: Artificial Sequence
<220> FEATURE:
<223> OTHER INFORMATION: MethylatedAdapter
<220> FEATURE:
<221> NAME/KEY: modified_base
<222> LOCATION: (8)..(32)
```

```
<223> OTHER INFORMATION: m5c
<220> FEATURE:
<221> NAME/KEY: modified_base
<222> LOCATION: (8)..(32)
<223> OTHER INFORMATION: m5c in replaces the 5' C in each CCGG tetramer
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 10
agttattncg gactgtncgg aagctgaatg ncgg                                34

<210> SEQ ID NO 11
<211> LENGTH: 34
<212> TYPE: DNA
<213> ORGANISM: Artificial Sequence
<220> FEATURE:
<223> OTHER INFORMATION: MethylatedAdapter
<220> FEATURE:
<221> NAME/KEY: modified_base
<222> LOCATION: (1)..(24)
<223> OTHER INFORMATION: m5c replaces 5' C in each CCGG tetramer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 11
ncggcattca gcttncggac agtncggaat aact                                34

<210> SEQ ID NO 12
<211> LENGTH: 36
<212> TYPE: DNA
<213> ORGANISM: Artificial Sequence
<220> FEATURE:
<223> OTHER INFORMATION: MethylatedAdapter
<220> FEATURE:
<221> NAME/KEY: modified_base
<222> LOCATION: (3)..(26)
<223> OTHER INFORMATION: m5c  5-methyl C replaces the 5' C in each CCGG
      tetramer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 12
tancggcatt cagcttncgg acagtncgga ataact                              36
```

```
<210> SEQ ID NO 13
<211> LENGTH: 34
<212> TYPE: DNA
<213> ORGANISM: Artificial Sequence
<220> FEATURE:
<223> OTHER INFORMATION: BisulfiteTreated

<400> SEQUENCE: 13
agttattctg gattgtctgg aagttgaatg ctgg                              34

<210> SEQ ID NO 14
<211> LENGTH: 34
<212> TYPE: DNA
<213> ORGANISM: Artificial Sequence
<220> FEATURE:
<223> OTHER INFORMATION: BisulfiteTreatedComplement

<400> SEQUENCE: 14
ctggtattta gtttctggat agtctggaat aatt                              34

<210> SEQ ID NO 15
<211> LENGTH: 36
<212> TYPE: DNA
<213> ORGANISM: Artificial Sequence
<220> FEATURE:
<223> OTHER INFORMATION: BisulfiteTreated

<400> SEQUENCE: 15
tactggtatt tagtttctgg atagtctgga ataatt                            36

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
ctggattgtc tggaagttga atgct                                        25

<210> SEQ ID NO 17
<211> LENGTH: 28
<212> TYPE: DNA
<213> ORGANISM: Artificial Sequence
<220> FEATURE:
<223> OTHER INFORMATION: ReversePrimer

<400> SEQUENCE: 17
gaccataaat caaagaccta tcagacct                                     28

<210> SEQ ID NO 18
<211> LENGTH: 30
<212> TYPE: DNA
<213> ORGANISM: Artificial Sequence
<220> FEATURE:
<223> OTHER INFORMATION: ReversePrimer

<400> SEQUENCE: 18
atgaccataa atcaaagacc tatcagacct                                   30

<210> SEQ ID NO 19
<211> LENGTH: 25
<212> TYPE: DNA
<213> ORGANISM: Artificial Sequence
<220> FEATURE:
<223> OTHER INFORMATION: McrA-F primer

<400> SEQUENCE: 19
```

```
gacgtctccc atgcatgttt ttgat                                              25

<210> SEQ ID NO 20
<211> LENGTH: 26
<212> TYPE: DNA
<213> ORGANISM: Artificial Sequence
<220> FEATURE:
<223> OTHER INFORMATION: McrA-R reverse primer

<400> SEQUENCE: 20
ctaatgtctt tattatccct aggaga                                             26
```

METHODS FOR DETECTION OF METHYL-CPG DINUCLEOTIDES

This application is a divisional of U.S. patent application Ser. No. 12/507,522, filed Jul. 22, 2009, which is incorporated herein by reference in its entirety.

This application claims benefit of U.S. Provisional Application No. 61/083,242 filed Jul. 24, 2008.

GOVERNMENT SUPPORT

This invention was made with Government support under contract number DE-AC02-98CH10886, awarded by the U.S. Department of Energy and sponsored in part by NIH grant 5U01AI056480-05. The Government has certain rights in the invention.

BACKGROUND OF THE INVENTION

Methylation of cytosine to form 5-methylcytosine occurs commonly in eukaryotic genomes. In mammalian cells, methylation of cytosine in CpG dinucleotide sequences (5-Me-CpG, 5mCpG, meCpG, or mCpG) plays a role in regulation of chromatin stability, gene regulation, parental imprinting and X-chromosome inactivation. Cytosine methylation is recognized as one of the most important epigenetic modifications in cells that affects a surprising number of physiological states. In particular it has been recognized that hypermethylation of cytosine in CpG-rich sequences located in promoter and/or other regulatory regions of genes (CpG islands) has a tremendous effect on gene expression. For example, hypermethylation of such regulatory regions has been correlated with cancer.

Esteller, et al. (Cancer Res. 2001:61, 3225-3229) have shown that specific hypermethylation profiles among several genes can be correlated to specific types of cancer. For example, hematological malignancies (lymphomas and leukemias) show hypermethylation of p73 and $p15^{INK4b}$, which hypermethylation is absent from many solid tumor tissues. Further, hypermethylation of the mismatch repair gene hMLH1 is restricted to tumor types characteristic of hereditary nonpolyposis colorectal cancer syndrome: colorectal, endometrial and gastric tumors with microsatellite instability.

Herman and Baylin (N.E.J. Med. 2003:349, 2042-2054) have reviewed gene silencing in cancer in relation to promoter hypermethylation. One of the specific points made in the review is the possibility that hypermethylation of specific gene regions can be used to identify very early stages in developing cancers. It has long been recognized for a variety of cancers that early detection provides significant long-term survival benefits. In modern medicine, considerable medical and basic scientific expertise has been and continues to be applied to the development of techniques, procedures and diagnostic assays that can be performed on specimens, particularly those that can be obtained non-invasively or in a minimally invasive manner, to identify at-risk individuals and to begin prevention/treatment evaluation and action. For example, sputum specimens can be used to identify aberrant methylation of specific genes in various stages of lung cancer (Belinsky et al. Proc. Natl. Acad. Sci. USA (1998) 95:11891-11896; Palmisano et al. Caner Res. (2000) 60:5954-5958). Similarly, prior to symptom onset, urine specimens could be used to provide cells indicating hypermethylation of genes that have been identified in association with bladder cancer. Likewise, examination of hypermethylation patterns in tissues obtained through minimally invasive procedures such as vaginal and cervical scrapings, gastric lavage specimens, and colon tissue could lead to early detection assays for vaginal, cervical and/or uterine cancer, esophageal or stomach cancers and colorectal cancers.

An ever increasing variety and sophistication of methods for detection of aberrant mCpG patterns are being applied to analysis of cytosine methylation. Several methods for analyzing DNA methylation patterns on a genome-wide scale have been developed, yet none have achieved wide spread acceptance. Rather than analyzing genome wide methylation patterns, many studies focus on specific gene regulatory regions, utilizing arrays carrying specific sequences which have previously been recognized as being related to the specific physiological condition being studied. Methods in general use combine the variety of approaches that have been developed over the years.

An early method relied on the use of methylation-sensitive and -insensitive restriction endonucleases. After cutting of DNAs with a pair of isoschizomers, Southern blotting or amplification analysis or a combination are used to assess methylation status of particular genetic loci. Other methods make use of modification or elimination of cytosine versus methyl-cytosine bases in DNA to assess methylation patterns (e.g., Tanaka et al., J. Am. Chem. Soc. 2007:129, 5612-5620; Frommer, et al., Proc. Natl. Acad. Sci. USA 1992:89, 1827-1831; Clark, et al. Nuc. Acids Res., 1994:22, 2900-2997). Some methods, such as "combined bisulfite restriction analysis" (COBRA) combine elimination of cytosine with restriction enzyme analysis (Xiong and Laird, Nuc. Acids Res. 1997:25, 2532-2534) to assess methylation status. Other methods combine cytosine modification/elimination with amplification analysis making use of specific amplification primers to match the variety of sequences that arise from bisulfite modification of cytosine residues, versus non-modification of methyl-cytosine (e.g., methylation-specific PCR (MSP), Herman et al., Proc. Natl. Acad. Sci. USA 1996:93, 9821-9826).

In addition, various methyl-cytosine binding ligands have been used to isolate mCpG-containing sequences. Such ligands include an antibody that requires single stranded DNA in order to bind mCpG sequences (Keshet et al. Nat. Genet. 2006:38, 149-153; Weber et al. Nat. Genet. 2005:37, 853-862); a methylated DNA binding protein domain (MBD) of MeCP2 (Cross et al. Nat. Genet. 1994:6, 236-244); a bivalent antibody-like construct of methyl-CpG binding domain protein 2 (MBD2) and human-$F_c$ (Gebhard, et al. Cancer Res. 2006:66, 6118-6128 and Gebhard, et al. Nuc. Acids Res. 2006:34, e82) and a complex of MBD2/MBD3L1 (Rauch, et al. Cancer Res. 2006:66, 7939-7947).

Kits making use of methyl-CpG binding proteins are now available for purchase from various sources (e.g., "Methyl-Collector"™ from Active Motif, Inc., Carlsbad, Calif.), as are kits for preparing bisulfite-treated DNA, a procedure which converts cytosine residues to uracil (e.g., EpiTect Bisulfite Kit from Epigenomics AG, Berlin, Germany), kits for Differential Methylation Hybridization (DMH-Epigenomics AG, Berlin), kits for Promoter Methylation Array and Methylation Promoter Polymerase Chain Reaction (PCR) (Panomics, Inc., Fremont, Calif.) and kits for "MethylLight" TaqMan® assays (EpiTect Quantitative MethylLight, Epigenomics AG, Berlin).

In the approaches utilizing proteins to enrich the fraction of sequences containing methyl-CpG sequences the affinity and specificity of the binding proteins are of considerable importance. If one wished to isolate such sequences from specimens in which the tumor or tumor progenitor cells represent a very small fraction of the total specimen, the affinity of the reagents is particularly important.

Methods to enrich the methyl-CpG sequences of a sample could simplify and enhance the accuracy of assays that might benefit from the combination of modification/elimination of cytosine residues, restriction analysis and methyl binding proteins.

For example, some propose to analyze specimens for the presence and prevalence of particular CpG sequences that are retained after bisulfite treatment of DNA, for instance, analyzing all remaining CGCG sequences. In this example, any retained CGCG sequence would indicate that the original DNA was doubly methylated prior to treatment ($-^{Me}CG^{Me}CG-$). The bisulfite reacted and amplified product (-CGCG-) could be analyzed through the use of cleavage with BstUI and the results related to specific sequences associated with particular cancers.

In bisulfite treated, amplified DNA, any remaining cytosine residues were originally methyl-cytosine residues. In the example of analyzing for retained CGCG sequences, only a fraction of the remaining cytosines in the entire bisulfite treated sample were originally in the doubly methylated CGCG sequence. Thus the cytosine residues remaining in CGCG may represent such a very small fraction of the remaining cytosine residues in the specimen that simple analytical methods involving binding with CpG binding ligands could prove ineffective. Thus, examination of specific methyl-CpG sequences would benefit from a procedure capable of enriching for the particular sequence in its methylated state. Embodiments of the present invention provide for enrichment of methyl-CpG sequences, particularly from DNA samples that were first treated to remove all non-methylated cytosine residues.

Another issue important to developing means for early diagnostic assays related to methylation status is illustrated in part in the above discussion. If one wished to analyze methylation status with respect to particular arrangements of CpG sequences (i.e., the "context" of the mCpG sequence) the above situation illustrates the difficulties. In the CGCG tetranucleotide there are four potential mCpG methylation states, unmethylated-CpGpCpG, singly methylated-$^{Me}$CpGpCpG or CpGp$^{Me}$CpG, and doubly methylated-$^{Me}$CpGp$^{Me}$CpG. After bisulfite treatment, the four states would yield UGUG, CGUG, UGCG and CGCG. Sequence analysis would not be capable of distinguishing whether the first three of the four product sequences arose from CGCG or TGTG, $^{Me}$CGCG or $^{Me}$CGTG, and CG$^{Me}$CG or TG$^{Me}$CG, respectively. The only clear result would be the one resulting in CGCG, which could only result from $^{Me}$Ce$^{Me}$CG.

This is also the case for the sequences having single mCpG methylation sites, but for which context is lost through bisulfite treatment and amplification. For example, CCGG, which has a single mCpG methylation site (C$^{Me}$CGG), which, after conversion of cytosines (e.g., by bisulfite treatment) and amplification is no longer CCGG, but would be TCGG. Thus, after bisulfite treatment and analysis, without methods of embodiments of the present invention, it would be difficult and likely impossible to know whether the sequence was originally T$^{Me}$CGG or was C$^{Me}$CGG. Other examples that would benefit from context determinative methods of the invention include any sequence that is CG rich that includes the mCpG dinucleotide.

An additional improvement in current methods would be afforded by providing additional mCpG-binding ligands. One aspect of the present invention provides an isolated, purified recombinant McrA protein (rMcrA) for specific binding of mCpG sequences found in the context of both C$^{Me}$CGG and $^{Me}$C$^{Me}$CGG. Clones and methods for expression, isolation and use of the rMcrA protein are disclosed herein.

SUMMARY OF THE INVENTION

One of the major problems standing in the way of the development of procedures to detect cells having an aberrant CpG methylation pattern when such cells are present as a very minor proportion of the sample cell population is the relatively low affinity of most Me-CpG binding ligands and their dependence upon having multiple Me-CpG sequences or a nearby specific sequence motif (e.g., Ho, et al. Mol. Cell. 2008:29, 525-531) to form a strong interaction with a DNA fragment. In samples having mostly normal cells, the aberrant Me-CpG sequences would likely be a very minor component of the total population of Me-CpG sequences in such samples, making their detection in the background of normally methylated and non-methylated sequences difficult. Thus, a method for enriching the methyl-CpG proportion of DNA fragments is provided.

In the method for enrichment of methyl-CpG sequences a DNA sample is prepared from a specimen and fragmented to a convenient size range. After ligation of a double stranded amplification primer cassette to the double stranded fragments, the DNA is treated under conditions suitable for conversion of all cytosine residues to uracil. The preferable conditions are those which are also suitable for preservation of all methyl-cytosine residues. The treated DNA fragments are then amplified, which converts all uracil residues to thymidine and all methyl-cytosine residues to cytosine. CpG dinucleotides remaining in the amplified fragments, all of which were originally Me-CpG sequences, are then methylated by incubation of the fragments with a CpG methylase, such as M.SssI. Since the only CpG's that remain in the preparation were originally methylated CpG dinucleotides, this restores the methylation state of the dinucleotide, but at an enriched level since the DNA had been amplified. Thus, the methylated amplified fragments can be readily collected using me-CpG binding ligands.

In advancing the state of our knowledge of the relationship between the methylation status of CpG residues in gene regulatory sequences and the physiological condition of cells, it is likely important to be able to analyze the actual context of me-CpG sequences found in GC-rich regions. Thus, in the preparations of DNA to be analyzed, methods for restoration of the actual sequence context would be advantageous.

For example, as discussed above, for the sequence CCGG, in procedures which convert cytosine residues to uracil, the context of the retained cytosine is lost. One aspect of the methods described here addresses preservation of context for the sequence C$^{Me}$CpGG. The methods (FIG. 2) comprise treatment of the DNA sample with MspI methylase which converts C$^{Me}$CpGG to $^{Me}$C$^{Me}$CpGG (and CCpGG to $^{Me}$CpGG). Upon conversion of cytosines to uracils and amplification, the sequences become CCpGG (and CTpGG). Methylation with HpaII methylase restores the original methylation pattern of the C$^{Me}$CpGG sequences. The rMcrA protein of the present invention, which binds C$^{Me}$CpGG sequences, can then be used to collect the DNA fragments having the preserved sequence.

More generally, the analysis of context of the Me-CpG dinucleotides in the sequences GCGC and CGCG can be accomplished, but not quite as elegantly at the present time. Methods for doing so require combinations of strategies similar to the above strategy with restriction enzyme analysis and/or methods to estimate the extent of methylation in the treated sample (i.e., such as LUMA).

For example, at the present time, the context of the sequence GCpGC versus G$^{Me}$CpGC can be analyzed, but appears to be limited to quantitation of retained GCpGC sequences which can be methylated (the LUMA assay could be used, for example) (FIG. 3A).

If a "3'-GCGC Methylase" and a "5'-GCGC Methylase" are discovered and are made available, the context of $G^{Me}CpGC$ could be preserved as shown in FIG. 3B. If a $^{Me}CpG$ binding ligand specifically recognizing $G^{Me}CpGC$ sequences becomes available, it could be used to bind and collect such preserved sequences.

As outlined in FIGS. 4A and 4B, the sequence CGCG can be analyzed for methylation state and context through a combination of steps which include fully methylating all CpG residues before or after converting cytosines to uracil followed by amplification and by restriction enzyme analysis.

In FIGS. 4A and 4B the CpG's of the DNA sample are either fully methylated prior to conversion of C's to U's (4A) or are converted to U's without prior methylation (4B). After amplification, a portion of each of the first two treated aliquots of the sample is then fully methylated with M.SssI and then all four portions are analyzed using BstUI cutting.

As shown in FIGS. 4A and 4B if full methylation is performed before conversion of C's to U's, the amplified DNA will be cut at each and every CpGCpG sequence originally present, or each segment of DNA will be fully resistant to BstU1 at all CpGCpG sequence, regardless of what the initial state of methylation of the original CpGCpG sequence. If conversion of C's to U's is performed first, followed by amplification and either no treatment or full methylation, the resulting products will be cut with BstUI only where the CpGCpG sequence was originally doubly methylated, or the segment of DNA will be fully resistant to BstUI cutting, but only the originally doubly methylated CpGCpG sequences remain as CGCG sequences whereas all of CpGCpG sequences are now altered. Thus the context of CpGCpG sequences can be determined.

In summary, through stepwise use of full methylation of CpG sequences, before or after conversion of C's to U's, followed by restriction enzyme analysis or quantification of retained methylation capable CpG sequences, the status and context of most CpG residues can be established. Focusing upon particular genes and their sequences through the use of specific probes or arrays simplifies the analysis. Building a compendium of relationships between CpG methylation state and context and its relationship to physiological states of the cells comprising the specimens can be useful to streamline diagnostic procedures.

Adding to the tools that are applicable to the analysis and determination of methylation status are the Me-CpG binding ligands. In the present invention, an agent which specifically binds 5'-$C^{Me}CGG$-3' DNA sequences is provided. The recombinant ligand, rMcrA protein, and methods for its production and use are provided. Vectors for production of the protein having suitable affinity tags are described.

DETAILED DESCRIPTION OF THE INVENTION

Figure 1A:
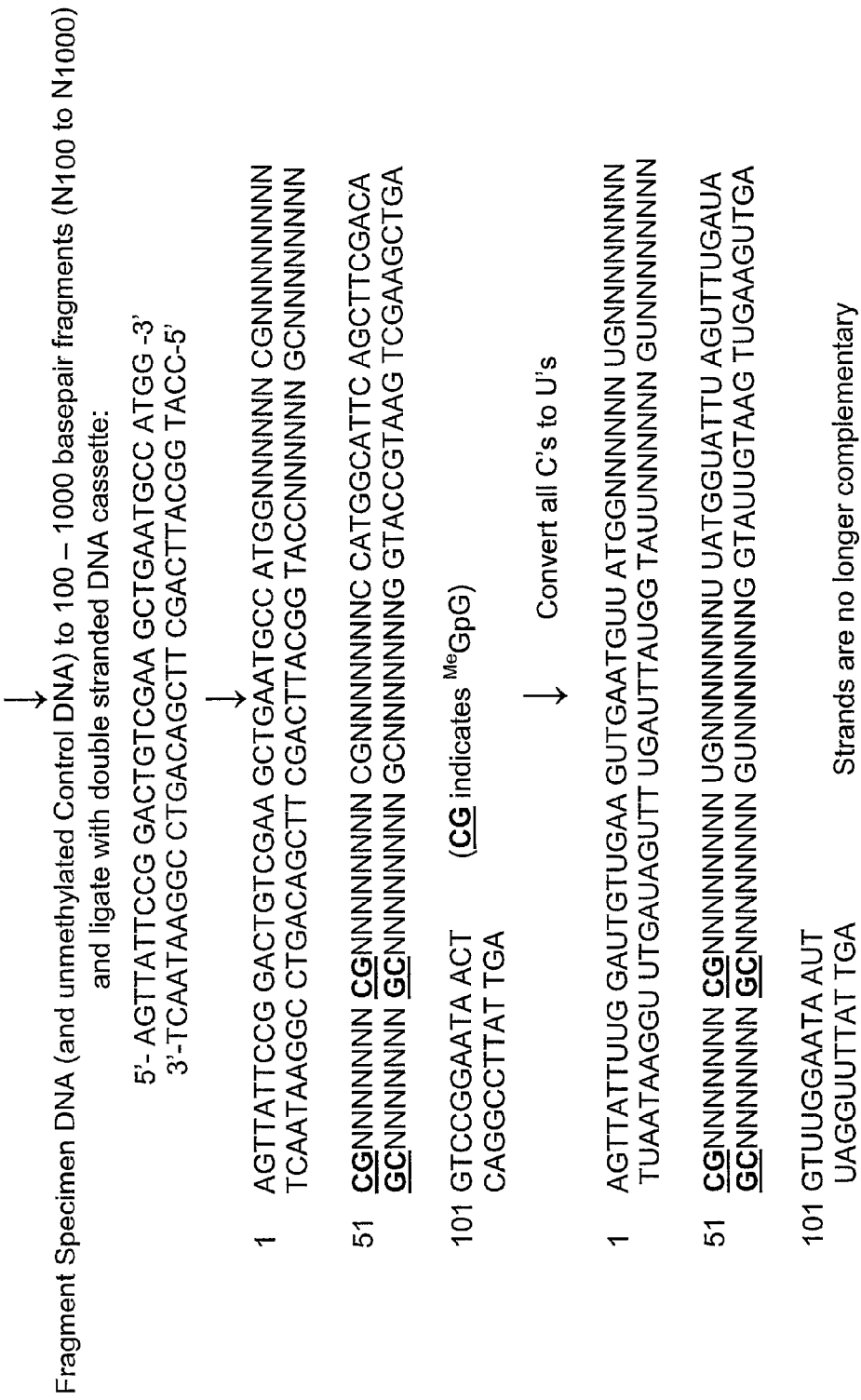
FIGS. 1A and 1B: A representation of the methods of the invention for enriching for methyl-CpG sequences in DNA reacted to convert cytosine residues to uracil residues SEQ ID NOS: 1, 2, 4 and 5.
Figure 1B:
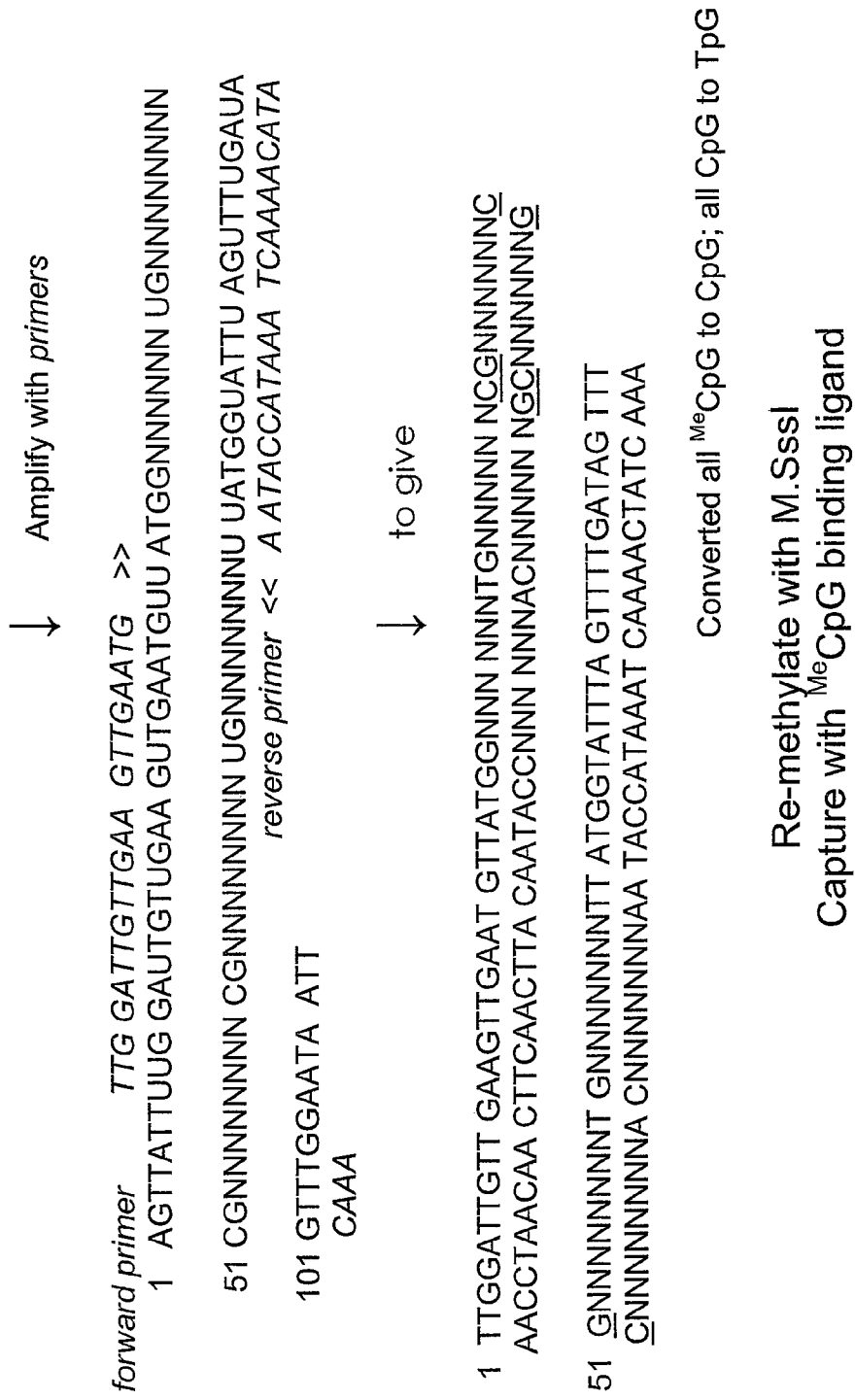
Figure 2:
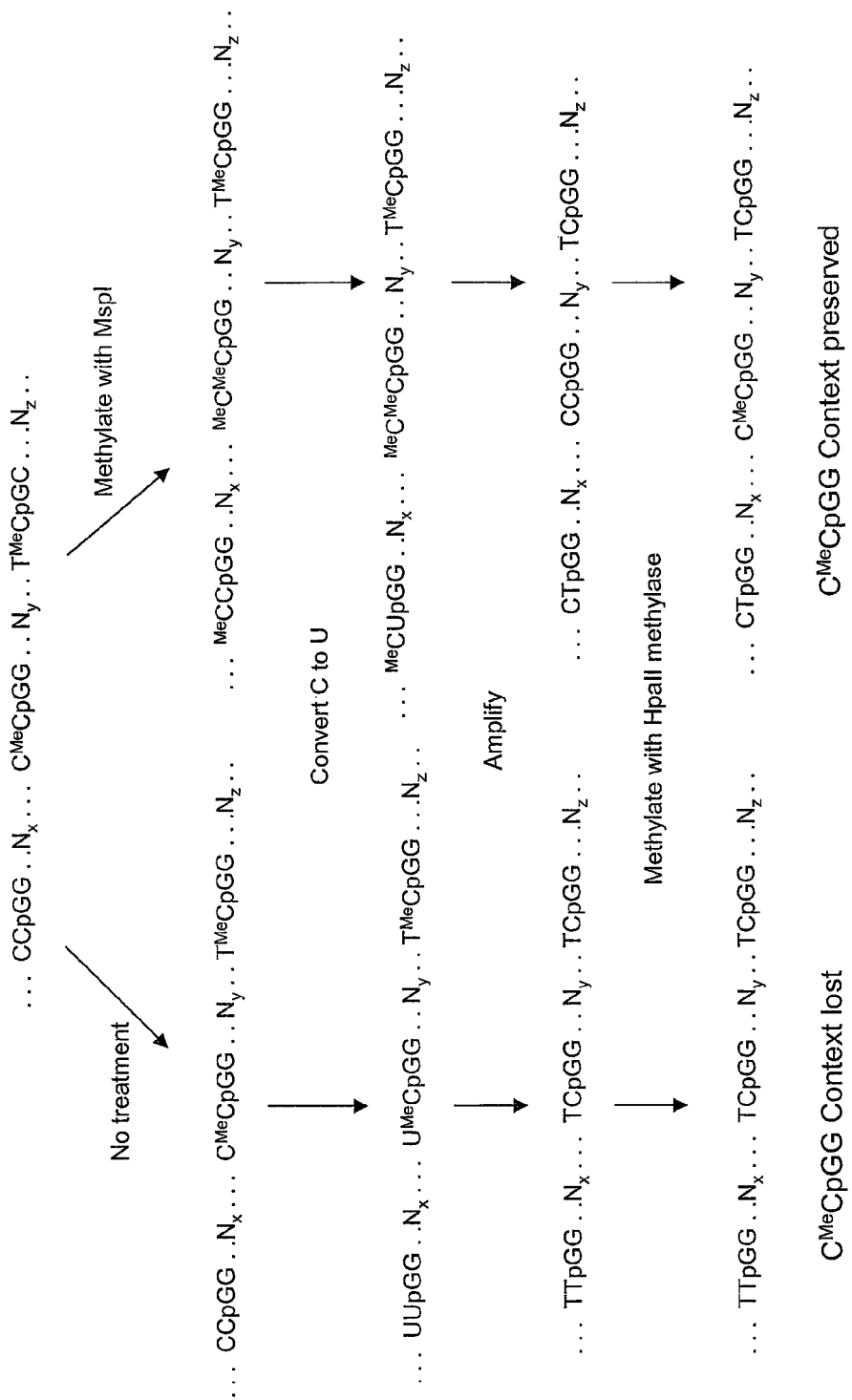
FIG. 2: A representation of the methods of the invention for preservation of the context of the methyl-CpG in the sequence CmCGG.
Figure 3A:
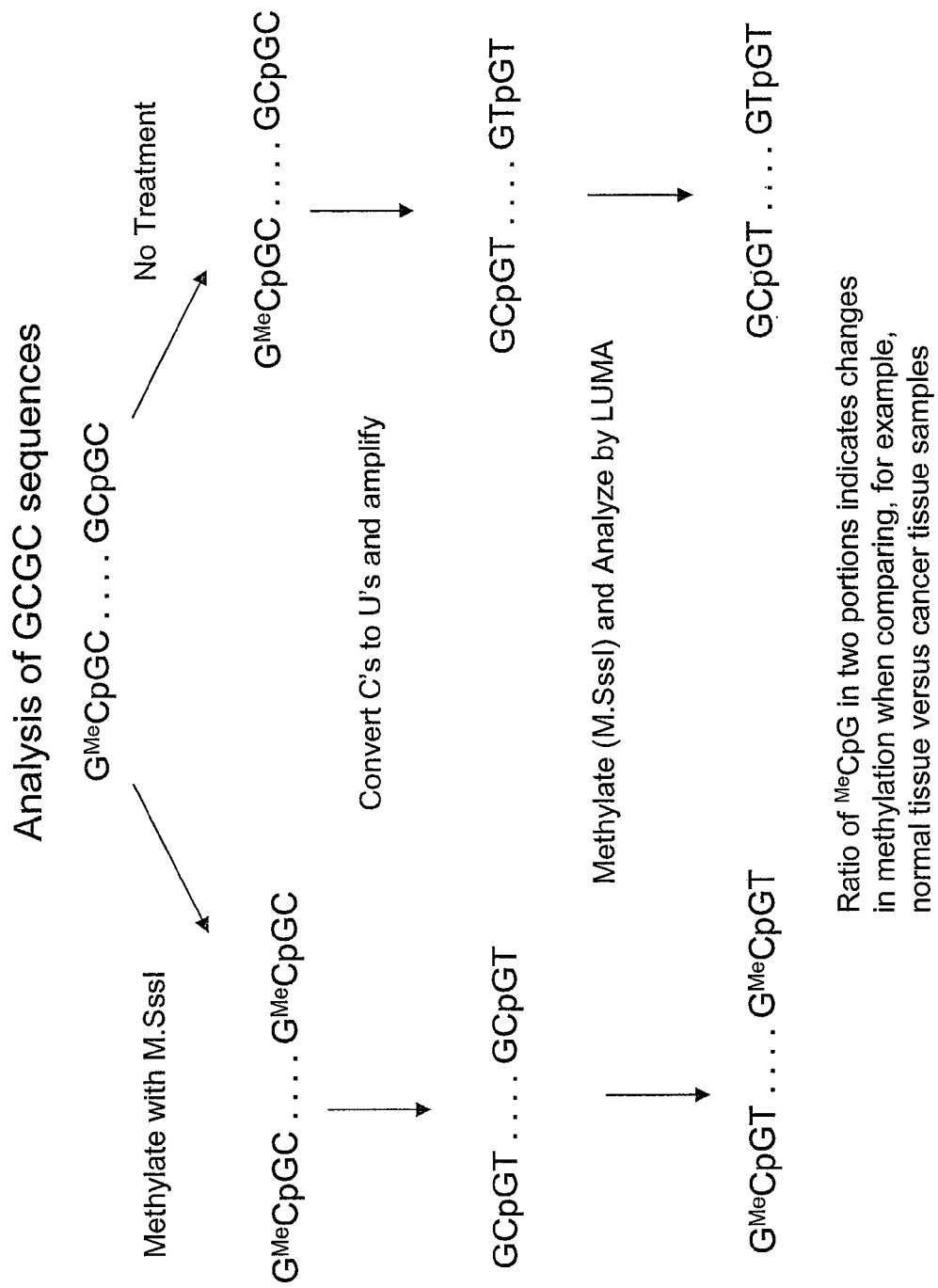
FIGS. 3A and 3B: A representation of analysis and possible analysis of methyl-CpG in the GmCGC sequences.
Figure 3B:
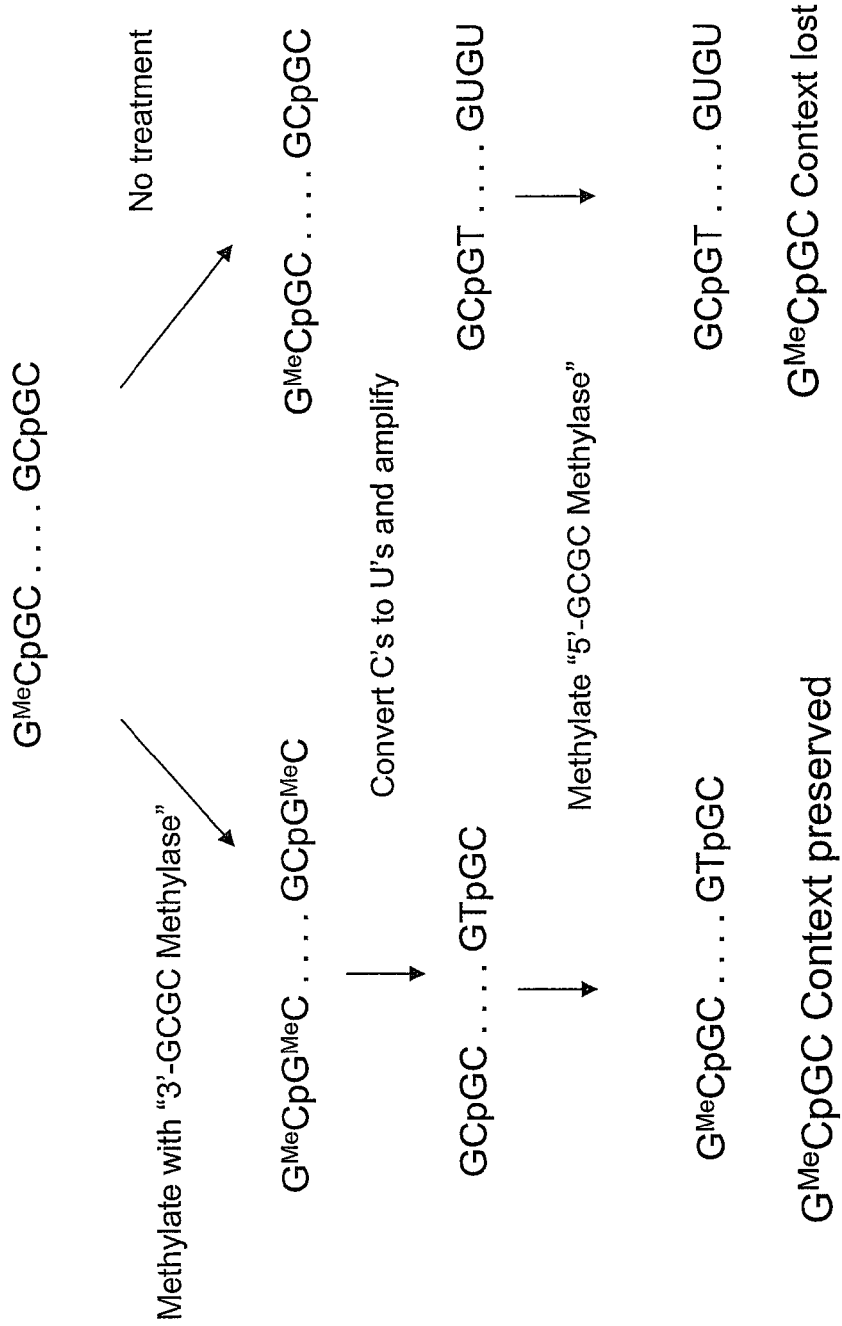
Figure 4A:
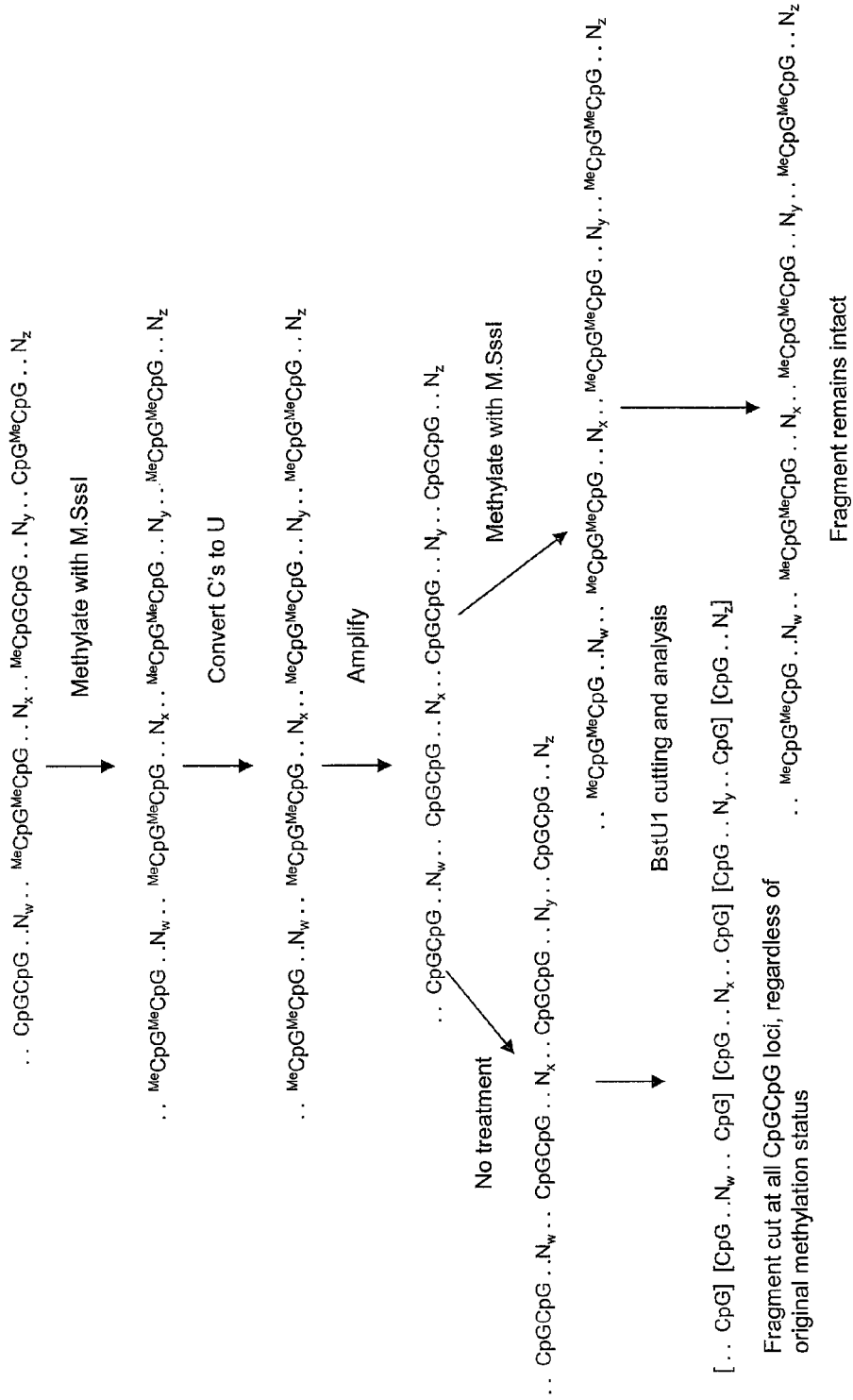
FIGS. 4A and 4B: A representation of analysis of methyl-CpG in the CGCG sequences.
Figure 4B:
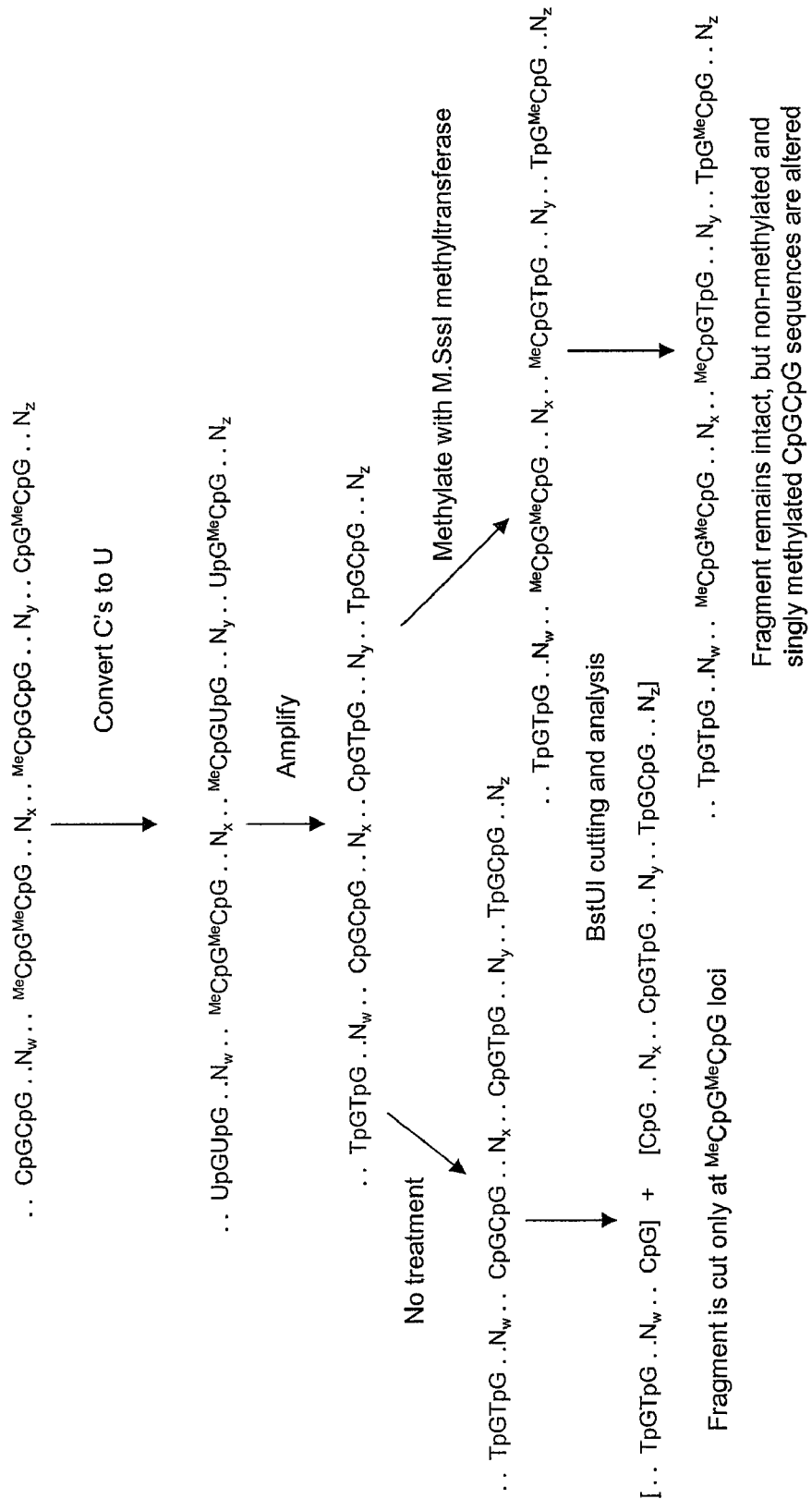

Enrichment of methyl-CpG sequences. A method for enriching the methyl-CpG sequences from a sample of DNA is provided. In the method for enrichment of methyl-CpG sequences a DNA sample is provided from a specimen and fragmented to a convenient size range. Optionally, either prior to or after ligation of an amplification cassette to both ends of the double stranded fragments, the DNA is contacted with a Me-CpG binding ligand and the fragments which are rich in Me-CpG are separated from fragments having few Me-CpG sequences. Ligation of an amplification cassette to the Me-CpG enriched fragment portion may facilitate ensuring that a molar excess of cassette to fragment ends had been used. After optional ligation of a double stranded amplification cassette to the double stranded fragments and/or after separation of Me-CpG rich fragments, the DNA is treated under conditions suitable for conversion of all cytosine residues to uracil. The preferable conditions are those which are also suitable for preservation of all methyl-cytosine residues. The treated DNA fragments, or subset thereof, are then amplified en masse using cassette-specific primers (or subset specific primers) designed to anneal to the converted DNA sequences (which, after conversion, contain no cytosine residues). This amplification step converts all uracil residues to thymidine and all methyl-cytosine residues to cytosine. All CpG residues remaining in the amplified fragments, all of which originally were Me-CpG sequences, are then methylated by incubation of the fragments with a CpG methylase. Since the only CpG dinucleotides that remain in the preparation were originally methylated CpG dinucleotides, this restores the original me-CpG dinucleotides, but enriches the methyl-CpG sequences because the DNA has been amplified. Thus, the enrichment provides for increased efficacy of collection of the me-CpG fragments by binding to me-CpG binding ligands.

In the method for enriching Me-CpG sequences from the DNA sample, the DNA is fragmented to a convenient size range. The fragmentation may be carried out by endonuclease digestion, by restriction endonuclease treatment or by mechanical methods such as sonication, nebulization and/or hydroshear.

Use of specific restriction endonucleases may take the form of selection of restriction endonucleases which are likely to leave most CpG island segments of the DNA intact. Examples include restriction enzymes that recognize and cleave at AT-rich sequences, including MseI, SSpI, Tsp509I, or AseI. Restriction enzyme fragmentation may produce either blunt ended fragments or fragments having sticky ends. A preferable restriction enzyme is MseI, which recognizes and cleaves the sequence TTAA, leaving a TA sticky end for later ligation of an amplification cassette. Optionally the digestion with restriction enzyme may be repeated to ensure full digestion.

Fragmentation of the DNA to a convenient size may be accomplished through mechanical means such as hydroshear, nebulization and/or sonication. DNA fragmented by these mechanical means may require repair of the ends of the DNA to provide blunt ended double stranded DNA fragments. In such circumstances it is preferable to repair the ends so that ligation with a blunt ended amplification cassette is facilitated.

A convenient size range for the double stranded fragments may be from about 100 base pairs to about 2000 base pairs, preferably from about 100 to about 1000 base pairs, even more preferably from about 100 to about 500 base pairs and most preferably from about 100 to about 250 base pairs.

Optionally, fragmented DNA may be separated into two or more portions on the basis of richness or density in Me-CpG regions (i.e., the number of Me-CpG dinucleotides per fragment of a particular size) using Me-CpG binding ligands. Some binding ligands have sufficient avidity to adequately bind, for separation purposes, DNA fragments having as few as one Me-CpG dinucleotide in about sixty base pairs. Solid supports bearing the MBD of NeCP2 can be used to fractionate the DNA fragments into sub-groups by stepwise elution with buffers of increasing salt concentrations (Cross et al, 1994). The Me-CpG DNA fragments are then further processed to enrich for me-CpG sequences of interest.

All double stranded fragments may be converted to amplifiable double stranded fragments by ligation of a double stranded amplification cassette to each end of the double stranded fragments. As noted, if restriction enzyme digestion yielded a sticky end, amplification cassettes are designed to have sticky ends that are complementary to the ends produced by the restriction enzyme. If the restriction enzyme produced blunt ended fragments or if the ends were repaired after mechanical fragmentation, the amplification cassettes are designed to have blunt ends to facilitate ligation.

If only a specific subset of DNA fragments are to be amplified, PCR amplification may be accomplished using sets of primers that are specifically designed to amplify only specifically selected genes or gene regions of interest, as in the MIRA assays of Rauch et al., 2005 and 2006.

The amplifiable fragments, or amplifiable subset of the DNA fragments are treated under suitable conditions to convert all cytosine residues to uracil while preserving all methyl-cytosine residues as methyl-cytosine. Methods are known in the art. A preferable method is through the use of bisulfite treatment. Such procedures are facilitated through materials and protocols which are readily generated in the laboratory or which are commercially available. This treatment produces a plurality of amplifiable fragments having no cytosine residues.

The cytosine-free amplifiable fragments are amplified. A preferable method is polymerase chain reaction (PCR) although other methods for exponential amplification or methods for linear amplification may be used. Amplification converts all uracil residues to thymidine and all methyl-cytosine residues to cytosine.

The amplified fragments are then methylated at all CpG dinucleotides, thus restoring the original pattern of meCpG dinucleotide sequences in the DNA sample. A useful reagent for accomplishing this step is the M.SssI methylase which is commercially available. Optionally this step may be repeated to ensure complete methylation of all remaining CpG dinucleotides.

The methylated amplified fragments are then contacted with a meCpG binding ligand to enrich for Me-CpG sequences. Examples of methylated DNA binding ligands include anti-me-CpG antibodies, methylated DNA binding protein domain (MBD) of MeCP2 (Cross et al. Nat. Genet. 1994:6, 236-244); a bivalent antibody-like construct of methyl-CpG binding domain protein 2 (MBD2) and human-$F_c$ (Gebhard, et al. Cancer Res. 2006:66, 6118-6128 and Gebhard, et al. Nuc. Acids Res. 2006:34, e82) and a complex of MBD2/MBD3L1 (Rauch, et al. Cancer Res. 2006:66, 7939-7947).

In addition, methylated DNA binding ligands include recombinant McrA (rMcrA) protein, disclosed herein.

All such methylated DNA binding ligands can be used for enriching for methyl-CpG sequences. The ligands can be attached to solid supports, such as plastic, including microtiter wells or test tubes, membrane or paper filters, beads, such as glass or magnetic beads. Attachment of the binding ligands to such solid supports facilitates collection of the methylated DNA and therefore facilitates enrichment for me-CpG sequences.

Preservation of $C^{Me}CpGG$ context. It is to be noted that the methods for enriching methyl-CpG sequences from a DNA sample may not restore the specific context of the Me-CpG dinucleotide. For example, if the original context of the me-CpG dinucleotide was $C^{Me}CpGG$, the enriched sequence would be $T^{Me}CpGG$ and not $C^{Me}CpGG$. Thus to preserve the context of $C^{Me}CpGG$ and to collect a population of DNA fragments containing the $C^{Me}CpGG$ sequence, another embodiment of the invention comprises providing a DNA sample, fragmenting the DNA to a convenient size range to form a plurality of double stranded fragments having a convenient size range, optionally ligating a double stranded amplification cassette to both ends of the fragments, optionally separating fragments rich in Me-CpG from fragments less rich in Me-CpG using a Me-CpG ligand or optionally separating fragments having $C^{Me}CpGG$ sequences from fragments lacking $C^{Me}CpGG$ sequences by contacting the fragments with an agent which specifically binds $C^{Me}CpGG$ sequences, methylating the fragments with a methylase which specifically methylates the C5 position of the 5' cytosine residue of $C^{Me}CpGG$ or CCpGG sequences to create a methylated DNA fragment population having $^{Me}C^{Me}CpGG$ and $^{Me}CCpGG$ sequences, treating the methylated DNA fragments under conditions suitable for conversion of all cytosine residues to uracil and which are also suitable for preservation of all methyl-cytosine residues, amplifying the fragments or subset thereof to form an amplified fragment population, methylating all remaining CCpGG DNA sequences to form a collection of DNA fragments having $C^{Me}CpGG$ sequences thereby preserving the context of the original $C^{Me}CpGG$ sequences.

The method for preserving the context of the original $C^{Me}CpGG$ sequences may further comprise concentrating said sequences by contacting the collection of DNA fragments have $C^{Me}CpGG$ sequences with an agent which specifically binds $C^{Me}CpGG$ sequences and separating bound DNA fragments from unbound fragments.

In this embodiment of the invention a convenient size range is from about 100 base pairs to about 2000 base pairs, preferably from about 100 to about 1000 base pairs, even more preferably from about 100 to about 500 base pairs and most preferably from about 100 to about 250 base pairs.

Fragmentation of the DNA of the sample to a convenient size can be accomplished through a variety of methods well known in the art, including endonuclease digestion, restriction endonuclease digestion and mechanical fragmentation as noted in the previously described embodiment of the invention.

Methods to preserve the context of $^{Me}CpG$ in $C^{Me}CpGG$ sequences may optionally include the ligation of the fragmented DNA to double stranded amplification cassettes as in the first embodiment of the invention.

Another option would be to separate double stranded DNA fragments that are rich in Me-CpG dinucleotides from those that are not rich in methylated CpG dinucleotides by use of Me-CpG ligands as noted in the first embodiment of the invention.

Further, the DNA fragments having $C^{Me}CpGG$ sequences may be optionally separated from fragments lacking the sequence through contact with a binding agent that specifically recognizes and binds $C^{Me}$CpGG sequences.

Methylation of $C^{Me}$CpGG and CCpGG sequences with a methyltransferase that specifically methylates the 5' cytosine of the sequences may be accomplished using MspI methyltransferase, which methylates the 5' cytosine of CCpGG or $C^{Me}$CpGG sequences to form a collection of DNA fragments having doubly methylated $^{Me}C^{Me}$CpGG sequences and singly methylated $^{Me}$CCpGG sequences. As developments in the field progress, any newly discovered methyltransferase capable of methylating the 5' cytosine residue of $C^{Me}$CpGG or CCpGG sequences may be used.

The methylated fragments are then treated under conditions which convert all cytosine residues to uracil, which conditions are suitable for preservation of all methyl-cytosine residues as methyl-cytosine. A preferable method is bisulfite treatment. Such procedures are facilitated through materials and methods which are readily available. The conversion does not alter $^{Me}C^{Me}$CpGG, but converts $^{Me}$CCpGG sequences to $^{Me}C^{Me}$CpGG.

The cytosine-free DNA fragments are then amplified, which converts all methyl-cytosine residues to cytosine (and all uracil residues to thymidine). Amplification can be accomplished through the use of PCR. If amplification cassettes were ligated to the plurality of double stranded fragments, primers specific to such amplification cassettes may be used. Alternatively, to amplify a subset of DNA fragments, PCR amplification may be accomplished using sets of primers that are specifically designed to amplify only specifically selected gene regions that are of interest as in the MIRA assays of Rauch et al. Lab. Invest. 2005:37, 853-862 and Rauch, et al., 2006, for example. Such regions of interest are those which have been identified through earlier work describing the relationship between aberrant methylation of CpG islands and various physiological conditions, including cancer. Alternatives to PCR methods may include linear amplification methods, including rolling circle amplification or other exponential amplification methods that are known in the art.

The amplified DNA fragments are then methylated with a methyltransferase which specifically methylates the 3' cytosine residue of CCpGG sequences to form $C^{Me}$CpGG sequences in the fragments, thus preserving the context of $C^{Me}$CpGG sequences. HpaII methyltransferase or any similar methyltransferase as may be identified may be used for this step.

To collect DNA fragments in which the $C^{Me}$CpGG context has been preserved, the methylated DNA fragments are contacted with an agent which specifically recognizes and binds $C^{Me}$CpGG sequences in DNA. Such an agent may be an anti-$C^{Me}$CpGG antibody or the recombinant McrA protein provided in the present disclosure. The binding agents ($C^{Me}$CpGG ligands) may be used to separate the DNA fragments having $C^{Me}$CpGG sequences from those fragments lacking such sequences. The separation may be facilitated by attachment of the ligand to solid supports, such as plastic, paper, membranes or beads. Alternatively, a "tagged" $C^{Me}$CpGG-binding ligand may be used to collect the fragments. In such circumstances, the binding ligand is prepared as a fusion protein wherein a "tag" element is fused in frame to either the amino or the carboxyl terminus of the binding ligand. The tag element has a binding partner that may be attached to the solid support, which then captures the tagged meCpG binding ligand and the bound DNA fragments.

5'-$C^{Me}$CpGG-3' binding agent. Another aspect of the present disclosure includes a ligand, or binding agent which specifically recognizes and binds to DNA containing 5'-$C^{Me}$CpGG-3' sequences. The ligand or agent optionally may also recognize and bind DNA containing 5'-$^{Me}C^{Me}$CpGG-3' sequences.

The binding agent of the present invention comprises recombinant McrA protein (rMcrA). DNA sequences encoding the rMcrA are provided as are plasmid expression constructs for generating the rMcrA protein.

The binding agent and plasmid expression constructs for encoding the binding agent may further include suitable affinity tag fusion partner to allow for capture of rMcrA, wherein the rMcrA capture may further result in capture of the DNA to which the rMcrA is bound. Suitable tags those well known in the art, such as the GST tag, S tag, T7 tag (e.g., EMD Biosciences, Madison, Wis.), the Strep tag (Schmidt and Skerra, Nature Protocols 2007:2, 1528-1535), FLAG (Stratagene, La Jolla, Calif.)), chitin binding domain (CBD) (New England Biolabs, Ipswich, Mass.), calmodulin binding protein (Vaillancourt et al., Met. Enz. 2000:326, 340-362; Stratagene, La Jolla, Calif.), and etc. Depending upon the specific tag, preferable embodiments include expression plasmids which are constructed such that tags are fused to the carboxyl terminal of rMcrA protein. The binding partners of the tags are attached to solid supports, such as plastic, paper, membranes or beads. When the rMcrA fusion protein—DNA fragment complex is contacted by the solid support bearing the tag binding partner, the Me-CpG DNA fragments are readily separated from the DNA fragments lacking the Me-CpG sequences.

EXAMPLES

Example 1

In experiments to enrich for DNA fragments from a DNA sample containing CGCG and particularly those containing Me-CpG sequences, DNA is isolated from cultured cells, for example normal human bronchial epithelial cells (NHBE) or cancer cell lines such as the lung cancer cell line A549.

The DNA is isolated by standard means and fragmented using the restriction enzyme MseI, which cleaves at TTAA, leaving TA overhangs. Alternatively the DNA is fragmented using sonication so as to form double stranded fragments of about 500 to 1000 base pairs in length. In the latter case the DNA fragment ends are repaired by standard means to ensure that all double stranded ends are blunt ended. Standard means includes the use of the DNATerminator End Repair Kit produced by Lucigen Corporation (Middleton, Wis.).

An amplification cassette is then ligated to both ends of the double stranded fragmented DNA. An amplification adapter of the present invention may include the double stranded cassette:

```
                                               (SEQ ID NO: 1)
    5'-AGTTATTCCG GACTGTCGAA GCTGAATGCC ATGG-3'

(SEQ ID NO: 2)
    3'-TCAATAAGGC CTGACAGCTT CGACTTACGG TACC-5'
```

Alternatively, if the DNA was fragmented with MseI, the amplification cassette may include:

```
                                               (SEQ ID NO: 1)
    5'-AGTTATTCCG GACTGTCGAA GCTGAATGCC ATGG-3'

(SEQ ID NO: 3)
    3'-TCAATAAGGC CTGACAGCTT CGACTTACGG TACCAT-5'
```

Bisulfite conversion of all cytosine residues of the ligated amplifiable DNA fragments is accomplished using standard reagents, such as kits supplied by Qiagen (Berlin, Germany).

The converted, cytosine free amplifiable DNA fragments are then amplified using primers specifically designed to the particular amplification cassettes which have all cytosine residues converted to uracil. A forward primer such as TTG GATTGTTGAA GTTGAATG (SEQ ID NO: 4) may be used. Reverse primers such as AAAC TATCAAAACT AAATAC-CATA A (SEQ ID NO: 5) or AAAC TATCAAAACT AAATACCATA ATA (SEQ ID NO.: 6) may be used.

Polymerase chain reaction (PCR) using standard cycles is employed to amplify the DNA fragments, or subset of fragments, and to thereby replace all uracils with thymidines and methyl-cytosines with cytosine residues.

All CpG dinucleotides are then converted to Me-CpG dinucleotides by treatment with CpG methyltransferase (M.SssI).

All DNA fragments having Me-CpG dinucleotides are captured using a Me-CpG binding ligand, such as an anti-Me-CpG antibody, MBD of MeCp2, a complex of MBD2/MBD3L1 or rMcrA disclosed herein or a combination thereof.

This method of the invention enriches for sequences in the DNA sample that originally contained methyl-CpG sequences.

Example 2

In bisulfite-treated or other DNA samples in which cytosine residues are converted to uracil while preserving the methyl-cytosine residues, the context of MeCpG in the sequence $C^{Me}CpGG$ can be preserved. The method involves methylating the DNA of the sample with a methyltransferase that specifically methylates the 5'-cytosine residue of CCpGG and $C^{Me}CpGG$ sequences. DNA, isolated from a sample, prior to conversion of cytosine residues to uracil under conditions which preserve methyl-cytosine residues, is treated with MspI methyltransferase under conditions to convert each CCpGG sequence to $^{Me}CCpGG$ and each $C^{Me}CpGG$ sequence to $^{Me}C^{Me}CpGG$. Standard reaction conditions may be used, such as those recommended by the suppliers such as New England Biolabs (Ipswich, Mass.). After methylation the methylation pattern of the DNA can be analyzed, particularly as it applies to $C^{Me}CpGG$ sequences.

In preserving the context of MeCpG in $C^{Me}CpGG$ sequences, DNA may be methylated with MspI methyltransferase prior to being fragmented or after being fragmented. Fragmented DNA may optionally be ligated to an amplification cassette prior to or after being methylated with MspI. DNA containing $C^{Me}CpGG$ sequences may be first separated from the bulk fragments by contact with a $C^{Me}CpGG$ binding ligand such rMcrA. Alternatively, such a binding ligand may be used after methylation and ligation of the DNA fragments.

After methylation of the DNA, all cytosine residues are converted to uracil using standard methods and reagents.

The treated DNA fragments are then amplified, converting all uracil residues to thymidine and all methyl-cytosine residues to cytosine.

A methyltransferase that converts the sequence CCpGG to $C^{Me}CpGG$ is then used to convert all remaining CCpGG to $C^{Me}CpGG$, thus preserving the context of the methyl-CpG in the sequence.

To collect the preserved $C^{Me}CpGG$ DNA, the DNA is contacted with the binding ligand, e.g., rMcrA, and the fragments having the preserved $C^{Me}CpGG$ sequences are separated from those lacking the sequence.

In the method to preserve the $C^{Me}CpGG$ sequences, DNA sample is provided from a specimen using standard procedures. The DNA is fragmented to create a plurality of double stranded DNA fragments having a convenient size using methods known in the art, such as endonuclease digestion, restriction enzyme digestion or mechanical fragmentation through sonication, nebulization and/or hydroshear.

A convenient size range is from about 100 to about 2000 base pairs, preferably from about 100 to about 1000 base pairs, more preferably from about 100 to about 500 base pairs and most preferably from about 100 to about 250 base pairs.

Double stranded amplification cassettes may be ligated to both ends of the double stranded DNA fragments to create a population of amplifiable DNA fragments. Optionally ligation with the amplification cassettes to form the population of amplifiable DNA fragments is carried out after the following steps.

The DNA fragments are treated with a reagent capable of converting all CCGG sequences to $^{Me}CCGG$ sequences and which is also capable of converting all $C^{Me}CGG$ sequences to $^{Me}C^{Me}CGG$ sequences. MspI methylase is a preferable reagent to accomplish this. Standard conditions such as those recommended by suppliers such as New England Biolabs (Ipswich, Mass.) may be used. The treatment may be repeated to ensure complete methylation.

The methylated DNA fragments are then amplified. An amplification cassette is ligated to both ends of the fragments (if this had not been done prior to methylation). Using PCR to amplify the fragments is carried out using the amplification cassette:

```
                                             (SEQ ID NO: 1)
5'-AGTTATTCCG GACTGTCGAA GCTGAATGCC ATGG-3'

(SEQ ID NO: 2)
3'-TCAATAAGGC CTGACAGCTT CGACTTACGG TACC-5'
```

Alternatively, if the DNA had been fragmented with MseI, the amplification cassette may include the double stranded cassette:

```
                                             (SEQ ID NO: 1)
5'-AGTTATTCCG GACTGTCGAA GCTGAATGCC ATGG-3'

(SEQ ID NO: 3)
3'-TCAATAAGGC CTGACAGCTT CGACTTACGG TACCAT-5'
```

Bisulfite conversion of all cytosine residues of the ligated DNA fragments is accomplished using standard reagents, such as kits supplied by Qiagen (Berlin, Germany).

The converted amplifiable DNA fragments are then amplified using primers specifically designed to the above amplification cassettes which have all cytosine residues converted to uracil. The forward primer is TTG GATTGTTGAA GTTGAATG (SEQ ID NO: 4). The reverse primer is AAAC TATCAAAACT AAATACCATA A (SEQ ID NO: 5) or AAAC TATCAAAACT AAATACCATA ATA (SEQ ID NO.: 6).

Ligation of an amplification cassette to the DNA fragments prior to MspI methylation may be used to provide a convenient experimental control in the form of CCGG sequences in the amplification cassette, which can be used to provide a way to amplify only the fully methylated cassette/DNA fragment species.

As presented above, the amplification cassette contains one CCGG sequence. For enhanced control two additional CCGG sequences could be incorporated as well. For example, the amplification cassettes comprising either SEQ ID NO: 1 and SEQ ID NO: 2 or SEQ ID NO: 1 and SEQ ID NO: 3 could be modified as follows (nucleotide substitutions are underlined and deletions are bracketed and underlined):

```
                                          (SEQ ID NO: 7)
5'-AGTTATTCCG GACTGTCCGG AAGCTGAATG CC[AT]GG-3'

(SEQ ID NO: 8)
3'-TCAATAAGGC CTGACAGGCC TTCGACTTAC GG[TA]CC-5'
or:
                                          (SEQ ID NO: 7)
5'-AGTTATTCCG GACTGTCCGG AAGCTGAATG CC[AT]GG-3'

(SEQ ID NO: 9)
3'-TCAATAAGGC CTGACAGGCC TTCGACTTAC GG[TA]CCAT-5'
```

Complete methylation with MspI converts the sequences to:

```
                                          (SEQ ID NO: 10)
5'-AGTTATT^MeCCGG ACTGT^MeCCGG AAGCTGAAT G^MeCCG G-3'

(SEQ ID NO: 11)
3'-TCAATAA GGCC^eMTGACA GGCC^eMTTCGACTTA CGGCC^eM-5'
and
                                          (SEQ ID NO: 10)
5'-AGTTATT^MeCCGG ACTGT^MeCCGG AAGCTGAAT G^MeCCG G-3'

(SEQ ID NO: 12)
3'-TCAATAA GGCC^eMTGACA GGCC^eMTTCGACTTA CGGCC^eMAT-5'
``` whereas partial methylation would create a mixture of molecules.

Bisulfite treatment and amplification would produce the following cassette sequences only from the fully methylated cassette/DNA fragments species:

```
                                          (SEQ ID NO: 13)
5'-AGTTATTCTG GATTGTCTGG AAGTTGAATG CTGG-3'

(SEQ ID NO: 14)
3'-TTAATAAGGT CTGATAGGTC TTTGATTTAT GGTC-5'
and
                                          (SEQ ID NO: 13)
5'-AGTTATTCTG GATTGTCTGG AAGTTGAATG CTGG-3'

(SEQ ID NO: 15)
3'-TTAATAAGGT CTGATAGGTC TTTGATTTAT GGTCAT-5'.
```

Any partially methylated cassettes would, have sequences that differ from the above. Using amplification primers specific for the amplification cassettes that had been completely methylated would, for the most part, result in amplification of only those cassette/fragment species that had been fully methylated during MspI methylase treatment. Such amplification primers may include:

Forward Primer:

```
5'-CTG GATTGTCTGG AAGTTGAATGCT-3'    (SEQ ID NO.: 16)
```

And Reverse Primers:

```
                                          (SEQ ID NO. 17)
5'-TCCA GACTATCCAG AAACTAAATA CCAG-3'
``` or

```
                                          (SEQ ID NO. 18)
5'-TCCA GACTATCCAG AAACTAAATA CCAGTA-3',
``` where the underlined nucleotides correspond to the retained cytosine residues (or complementing G residues) which resulted from the complete methylation step. Under appropriate conditions, any partially methylated cassette/fragment species would hybridize poorly with these amplification primers and would be less readily amplified, thus selecting for the DNA fragments that had been fully methylated at CCGG sequences.

Those skilled in the art clearly recognize that many other configurations of amplification cassettes and primers would substitute for the examples suggested above, which are presented as a means of exemplification but which are not intended to preclude the use of other appropriate cassettes and primers. Appropriate cassettes are double stranded or partially double stranded DNA sequences of about 20 to about 40 base pairs in length, which double stranded fragments have ends that are compatible for ligation to the double stranded ends of the conveniently sized DNA fragments of the sample. Appropriate amplification primers are single stranded DNA sequences complementary to the C to U converted amplification cassette sequences, and have a length of about 20 to about 35 bases. Appropriate cassettes and primers may further include sequences that are recognized by specific restriction endonucleases so as to add such cutting sites to the amplified DNA species to facilitate cloning and other procedures.

Other appropriate amplification strategies may include the use of primers that are chosen to be complementary to specific gene regions of the DNA being studies. For example, sequences from regions previously associated with the physiological condition of interest may be chosen for use as amplification primers.

Polymerase chain reaction (PCR) using standard cycles is employed to amplify the DNA fragments and to thereby replace all uracils with thymidines and methyl-cytosines with cytosine residues. After amplification, the sequences that were originally $C^{Me}CpGG$ and which were then doubly methylated ($^{Me}C^{Me}CpGG$) are now CCpGG and the sequences that were originally CCpGG are now CTpGG.

Treatment of the amplified fragment population with a methylase that methylates the 3' cytosine of CCpGG restores the context of the original $C^{Me}CpGG$ sequences. Appropriate methylases include HpaII methylase and any others which may be identified having that specificity. Reaction conditions recommended by suppliers of HpaII methylase, such as New England Biolabs (Ipswich, Mass.) can be used.

Example 3

Collection of DNA Containing $C^{Me}CpGG$ Sequences

At any point in the to preserve the context of $C^{Me}CpGG$ sequences, the isolated recombinant McrA protein (rMcrA) could be used to preferentially select DNA fragments having either $C^{Me}CpGG$ or $^{Me}C^{Me}CpGG$ sequences from DNA fragments lacking such sequences. rMcrA proteins, fully described in the following examples, having affinity tags are particularly, useful for these purposes. The preservation of the context of the $C^{Me}CpGG$ sequences permits the rapid separation of fragments having such sequences from those lacking the tetranucleotide sequence.

Example 4 rMcrA Protein

Summary: Expression strains of *Escherichia coli* BL21 (DE3) overproducing the *E. coli* m$^5$C McrA restriction protein were produced by cloning the mcrA coding sequence behind a T7 RNA polymerase promoter. The recombinant mcrA minus BL21(DE3) host produces active McrA as evidenced by its acquired ability to selectively restrict the growth of T7 phage containing DNA methylated in vitro by HpaII methylase.

The mcrA coding region contains several non-optimal *E. coli* triplet codons. Addition of the pACYC-RIL tRNA encoding plasmid (Stratagene, La Jolla, Calif.) to the BL21(DE3) host increased the yield of recombinant McrA (rMcrA) upon induction about 5- to 10-fold. rMcrA protein expressed at 37° C. is insoluble but a significant fraction is recovered as soluble protein after autoinduction at 20° C. (Studier, Prot. Exp. Purif. 2005:41, 207-234).

rMcrA protein, which is predicted to contain a Cys$_4$-Zn$^{++}$ finger and a catalytically important histidine triad in its putative nuclease domain, binds to several metal chelate resins even in the absence of a poly-histidine affinity tag. This feature was used to develop an efficient protocol for the rapid purification of nearly homogeneous rMcrA. The native protein is a dimer with a high α-helical content as measured by circular dichroism analysis.

Under all conditions tested purified rMcrA does not have measurable nuclease activity on HpaII methylated (C$^{Me}$CGG) DNA, although the purified protein does specifically bind HpaII methylated DNA.

*E. coli* McrA protein: DNA containing C$^5$-methylcytosine (MeC, $^{Me}$C, mC, methyl-C) is restricted by the Mcr (for modified cytosine restriction) system which is identical to the previously described Rgl (for restricts glucose-less phage) restriction system that blocks the growth of T-even phages, but only when they contain 5-hydroxymethyl cytosine in their DNA, i.e., when their 5-hydroxymethylcytosine residues are not glucosylated. Later work further subdivided the Mcr system into two genetically distinct regions: McrA (equal to RglA) on an easily excisable but defective lambdoid prophage element e14 located at 25 min on the *E. coli* K-12 chromosome and McrB (or RglB) at map position 99 min in a region that includes the EcoK restriction/modification and Mrr systems (Raleigh, et al. Nuc. Acids Res. 1988:16, 1563-1575; Raleigh, et al. Genetics 1989:122, 279-296).

McrA recognizes DNA containing C$^5$-methylcytosine or C$^5$-hydroxymethylcytosine while McrB also recognizes DNA containing N$^4$-methylcytosine. Early studies showed that DNAs methylated by M.HpaII (C$^{Me}$CGG), M.Eco18311 (Cm$^5$CSGG where S is C or G) and M.SssI ($^{Me}$CG) are restricted by the McrA system and further studies demonstrated that clones expressing the McrA open reading frame conferred both McrA and RglA phenotypes on a mcr minus host (Raleigh et al, 1989). However, because the McrA protein has never been purified its precise sequence preferences and its mode of action remain unclear although it is generally believed to be a member of the ββα-Me finger superfamily of nucleases acting specifically on mC containing DNA. McrA also contains a H—N—H motif common to homing endonucleases as well as many restriction and DNA repair enzymes. The core ββα-Me domain of McrA (residues 159 to 272 of the 277 amino acid long polypeptide) was modeled by Bujnicki and coworkers (Mol. Microbiol. 2000:37, 1280-1281) using a protein sequence threading approach. This region contains three histidine residues (H-228, 252, and 256) predicted to coordinate a Mg$^{2+}$ ion, as well as four cysteine residues (C-207, 210, 248, and 251) which form a putative zinc finger, most likely involved in coordinating Zn$^{2+}$ or some other divalent metal ion to help stabilize the protein's structure.

While McrA is predicted to function as a nuclease this has never been demonstrated and to date the mechanism for biological restriction of modified phage or plasmid DNAs by McrA is not known. Furthermore, although a slightly N-terminal truncated form of the polypeptide has been cloned in an expression vector (Hiom and Sedgwick, J. Bacteriol. 1991: 173, 7368-7373; Ramalingam, et al. J. Biosci. 1992:17, 217-232), full length, active McrA protein has not been purified. The present invention includes methods for the cloning, expression, purification and use of full-length, biologically active rMcrA.

All attempts to demonstrate that rMcrA is a nuclease acting on $^{Me}$C containing DNA have failed but electrophoretic mobility shift analysis demonstrates that purified rMcrA interacts specifically with DNA fragments containing C$^{Me}$CGG sequences.

Cloning McrA: *E. coli* K12 W3110 (mcrA$^+$) genomic DNA was used as template to PCR amplify the 833 bp (Hiom and Sedgwick, 1991) McrA coding sequence with McrA-Forward (McrA-F) primer 5'-GACGTCTCCC ATGCATGTTTTTGAT-3' (SEQ ID NO.:19) and McrA-Reverse (McrA-R) primer 5'-AGAGGATCCC TATTATTTCTGTAATC-3' (SEQ ID NO.:20), respectively and PfuTurbo C$_x$ Hotstart DNA polymerase (Stratagene, La Jolla, Calif.). Bases in the primers complementary to the McrA coding sequence are underlined. McrA-F contains a unique BsmBI recognition sequence while McrA-R contains a unique site for BamHI (both shown in italics) which were added to facilitate directional cloning of the digested DNA into the unique NcoI and BamHI sites of a pET28 expression plasmid. The initial amplicons were purified and blunt end ligated into pZERO-2 cut with EcoRV. Following electroporation into *E. coli* TOP10 cells (Stratagene) several pZERO-McrA (Kan$^R$) plasmids were purified and the correct sequence of the inserts verified by DNA sequencing using standard M13 primers flanking the cloning site. One of the correct recombinant plasmids was digested with BsmBI and BamHI to release a full-length McrA fragment having ends compatible with those of NcoI, BamHI digested pET28. Following gel purification and elution, the McrA containing fragment was directionally cloned into pET28, previously digested with NcoI and BamHI, using standard ligation conditions and subsequently electroporated into TOP10 cells. The resulting pET-rMcrA plasmid DNA was used to transform BL21(DE3) cells with and without the pACYC-RIL tRNA encoding (Cl$^R$) plasmid. All transformants were plated on 2×YT agar plates supplemented with 50 µg/ml Kanamycin (Kan) or with 50 µg/ml Kan and 25 µg/ml Chloramphenicol (Cl) as needed. The pRIL tRNA plasmid: argU(AGA,AGG), ileY(AUA) and leuW(CUA), was isolated from Stratagene BL21-CodonPlus McrA+ cells (Strategies Newsletter 14.2, p. 50-53) and then moved into BL21(DE3) to place the plasmid in an McrA minus background. This BL21(DE3) mcr$^-$/pRIL$^+$ strain was kindly provided by F. W. Studier (BNL).

McrA expression: Expression of McrA was initially tested in BL21(DE3) with and without the pRIL tRNA plasmid by addition of 0.5 mM IPTG to mid log phase cells in 2×YT medium or by growth to saturation in ZYM 5052 autoinduction medium at 37° C. and 20° C. (Studier, 2005). These media contained 100 µg/ml Kan and 25 µg/ml Cl as needed and were supplemented with 30 µM ZnSO$_4$. Induction and solubility of the expressed McrA protein was followed by SDS-PAGE. Expression of rMcrA was increased≧5-fold by the presence of the pRIL plasmid. This strain was used for all future experiments. Recombinant McrA (rMcrA) expressed at 37° C. was insoluble but a sizeable fraction was soluble if expression was done at 20° C. We therefore chose to induce protein expression at 20° C. and for ease we also used auto-inducing conditions.

Shaking cultures (100 to 200 ml in 0.5 or 1 L flasks) were initially started at 37° C. by addition of 1 ml of an overnight culture in 2×YT and moved to 20° C. once growth became visible. Cells were harvested after 48 h by centrifugation at 5,000 g for 10 min at 4° C., washed with 1/10 vol. 1×PBS, recentrifuged and the cell pellets (~1.2 g/50 ml culture) stored frozen at −20° C.

rMcrA purification: Cell pellets were thawed and resuspended in 10 ml of LEW buffer (50 mM NaPO4, pH 8.0; 300 mM NaCl). Lysozyme (20 mg/ml) was added to a final concentration of 100 μg/ml and the cells were frozen and thawed 3× using a dry ice-ethanol slurry to promote lysis. The extract was sonicated 4-6 times in 30 sec bursts alternated with chilling on ice to reduce viscosity and then centrifuged at 10,000 rpm for 10 min at 4° C. The pellet was resuspended in 5 ml of LEW and recentrifuged at 10,000 rpm for 10 min at 4° C. The soluble fractions were pooled and mixed for 30 min at 4° C. with 0.5 gm of PrepEase High-Yield Ni-chelate resin (USB, Cleveland, Ohio) pre-equilibrated with LEW. The resin was pelleted by centrifugation (5,000 rpm for 5 min) and batch washed consecutively with 15 ml LEW, LEW+700 mM NaCl (1 M final NaCl concentration), and LEW+2 mM imidazole before pouring into a small 1 cm i.d. column. The settled resin was washed with 25 ml of LEW+2 mM imidazole then with LEW+100 mM imidazole to elute rMcrA collecting 2 ml fractions. All chromatography steps were carried out at room temperatures. Peak fractions were pooled, diluted with an equal volume of 10 mM NaPO$_4$, pH 8.0, and passed through a 5 ml bed of SP-Sepharose Fast Flow (Pharmacia Biotech, Uppsala, Sweden) pre-equilibrated with 0.5× LEW. The column (1 cm i.d.) was washed with ~25 ml 0.5× LEW and the bound rMcrA eluted with LEW. Peak fractions were pooled and stored at 4° C. At this stage the protein was ≧99% pure as estimated by Coomassie Blue staining following SDS-PAGE.

Biological Activity of rMcrA: To test for biological activity T7 phage containing normal, non-methylated or in vitro HpaII methylated T7 DNA was titered on BL21(DE3) pRIL cells with and without pET-rMcrA. The presence of pET-rMcrA reduced the efficiency of plating (EOP) of the phage containing methylated DNA approximately a thousand-fold compared to the EOP on this same host containing a similar pET28 vector with a non-related recombinant gene insert at the some position. This reduction in EOP was selective and not seen with in vitro packaged T7 phages containing non-methylated DNA. From these results we concluded that rMcrA is biologically active.

rMcrA is not a MeC-specific nuclease: Numerous attempts to find conditions under which rMcrA would digest HpaII methylated T7 DNA or pGEM3 plasmid DNA in vitro were unsuccessful. Among the parameters tested were different buffers (New England Biolabs #1, #2, #3 and #4; 50 mM K glutamate, pH 6.0; LEW and 20 mM Hepes, pH 7.2, 300 mM NaCl) and addition of 1.5 or 3 mM $Ca^{2+}$; $Cd^{2+}$; $Cu^{2+}$; $Fe^{2+}$; $Mg^{2+}$; $Mn^{2+}$; $Ni^{2+}$ or $Zn^{2+}$ ions; as well as addition 3 mM ATP or GTP or 10 μM S-adenosylmethionine to the standard NEB restriction buffers. While we cannot rule out the possibility that rMcrA was inactivated during purification this seems unlikely given the ability of the protein to restrict methylated phage DNA and to selectively bind HpaII methylated DNA (see below).

rMcrA selectively binds HpaII methylated DNA: The DNA-binding properties of rMcrA were examined using fragments of unmethylated and HpaII methylated T7 DNA by Electorphoretic Mobility Shift Assays (EMSAs). The mobilities of the HpaII methylated fragments were significantly retarded in the presence of even small amounts of rMcrA (e.g., ≦0.5 rMcrA/$C^{Me}$CGG site/fragment). The addition of rMcrA had no effect on the mobility of the non-methylated fragments until very high ratios of protein to DNA were used. Furthermore, the addition of rMcrA resulted in the appearance of two distinct shifted products for each of the smaller fragments, suggesting multiple independent binding events on the 7 or 15 $C^{Me}$CGG sequences in the smaller fragments analyzed.

Separate experiments demonstrated that binding of rMcrA to HpaII methylated T7 DNA does not modify the methylcytosine ring as occurs upon binding of the *Arabidopsis thaliana* proteins DEMETER (DME) and repressor of silencing (ROS1) (Agius et al. Proc. Natl. Acad. Sci. USA 2006: 103, 11796-11801; Zhu, et al. Curr. Biol. 2007:17, 54-59; and Morales-Ruiz, et al. Proc. Natl. Acad. Sci. USA 2006:103, 6853-6858). These closely related DNA glycosylase domain containing proteins remove 5-methylcytosine from the DNA backbone and then their lyase activities cleave the resulting abasic site by successive β- and δ-elimination reactions.

If McrA has a similar activity it could account for its known restriction of methylated DNA and initiation of a SOS response following in vivo induction of HpaII in mcrA$^+$ cells. To rule out this possibility we treated rMcrA reacted DNA with proteinase K, EDTA and SDS followed by phenol/chloroform extraction and demonstrated that the DNA was still resistant to cutting by HpaII but sensitive to cutting with MspI which cleaves the same sequence even when the internal cytosine is 5-methylated.

rMcrA binds to other methylated DNA sequences: For these EMSAs, T7 DNA was modified by HpaII and the other six methyltransferases listed in Table 1. Most of these enzymes with the exception of dam methyltransferase have more than 50 sites in T7 DNA. Interestingly no shift products were observed for any of these non-HpaII methylation patterns. However, dual methylation by HpaII and MspI ($m^5Cm^5CGG$) did not prevent binding. These observations are consistent with and extend the previous finding about the specificity of McrA, which had been based solely on in vivo studies (Heitman and Model, 1987; Raleigh and Wilson, 1986; and Raleigh et al, 1988). However, they still do not identify conclusively the minimal sequence or number of sites needed for McrA binding nor explain its mode of action in vivo. Presumably, McrA acting simply as a DNA binding protein could interfere with methylated phage development or plasmid maintenance. It is possible that bound McrA interacts with some other *E. coli* protein(s) to cause cleavage in vivo at methylated HpaII sites. Attempts to demonstrate that rMcrA can act in concert with McrBC to cause cleavage at methylated HpaII sites have been unsuccessful.

TABLE 1

| Methylase | Sequence | sites in T7 | rMcrA binding |
|---|---|---|---|
| AluI | 5'-AG$^{Me}$CT-3' | 140 | No |
| Dam | 5'-G$^{Me}$ATC-3' | 6 | No |
| HaeIII | 5'-GG$^{Me}$CC-3' | 68 | No |
| HhaI | 5'-G$^{Me}$CGC-3' | 103 | No |

TABLE 1-continued

| Methylase | Sequence | sites in T7 | rMcrA binding |
|---|---|---|---|
| HpaII | 5'-C$^{Me}$CGG-3' | 58 | Yes |
| MspI | 5'-$^{Me}$CCGG-3' | 58 | No |
| MspI + HpaII | 5'-$^{Me}$C$^{Me}$CGG-3' | 58 | Yes |
| TaqI | 5'-TCG$^{Me}$A-3' | 111 | No |

Minimum number of C$^{Me}$CGG sites for rMcrA binding: Investigations with the HpaII methylated T7 DNA fragments showed that fragments with as few as 7 C$^{Me}$CGG sites were efficiently bound by rMcrA protein. When the ratio of rMcrA:C$^{Me}$CGG was about 0.5, a fragment having 7 such sequences was completely mobility shifted in the EMSA, suggesting that fewer than 3 such sequences is required in a fragment that is approximately 3-4 kb in size. Recent results suggest that as few as two C$^{me}$CGG sites may be sufficient for effective binding.

Because the rMcrA protein does not bind HhaI methylated DNA (G$^{Me}$CGC) the rMcrA protein provides a way to isolate a subset of the $^{Me}$CpG sequences bound by the methyl binding domains of the MeCP2 and MBD2 proteins which have previously been used to separate highly methylated CpG regions from non-methylated regions.

Fusion of rMcrA to affinity tags: Fusing rMcrA to appropriate (non-His tag) affinity tags permits its use in matrix-assisted binding of fragments containing C$^{Me}$CGG sequences. Such tags include the GST tag, S tag, T7 tag (e.g., EMD Biosciences, Madison, Wis.), the Strep tag (Schmidt and Skerra, Nature Protocols 2007:2, 1528-1535), FLAG (Stratagene, La Jolla, Calif.)), chitin binding domain (CBD) (New England Biolabs, Ipswich, Mass.), calmodulin binding protein (Vaillancourt et al., Met. Enz. 2000:326, 340-362; Stratagene, La Jolla, Calif.), and etc.

Sequences for the affinity tags are optionally added to the expression vector described herein above in frame with either the amino terminus or the carboxyl terminus of the encoded rMcrA protein. Alternatively, the insert in the expression vector described herein can be excised (or re-amplified using an appropriate set of primers) and inserted into vectors containing such tags such that the tag and rMcrA protein are in-frame, with the tag optionally fused to the rMcrA protein at the amino or the carboxyl terminus. Fusion of the tag at the carboxyl terminus of the rMcrA protein is a preferable configuration for most affinity tags.

Biotinylation of the rMcrA protein can provide an alternative to encoding a fusion protein of the rMcrA and affinity tag. The purified rMcrA protein can be modified with a biotinylation reagent, such as a biotin-NHS ester reagent (e.g., NHS-PEO4 kit from Pierce, Rockford, Ill.) or biotin sulfo-NHS ester (e.g., Chromalink, SoluLink, San Diego, Calif.). The biotinylated rMcrA (and the DNA to which it binds) is then easily bound to a solid support carrying its binding partners avidin or streptavidin.

The invention claimed is:

1. An agent which specifically binds 5'-$C^{Me}$CpGG-3' DNA sequences, in vitro, comprising recombinant full-length, active McrA protein (rMcrA) or fusion derivative thereof, which protein or derivative thereof is more than about 90% pure.

2. The agent according to claim 1 in which the recombinant full-length, active McrA protein derivative is a fusion protein of rMcrA and an affinity tag.

3. The agent according to claim 2 wherein the affinity tag is fused in-frame to the amino terminus of rMcrA.

4. The agent according to claim 2 wherein the affinity tag is fused in-frame to the carboxyl terminus of rMcrA.

5. The agent according to claim 2 wherein the affinity tag is selected from the group consisting of GST, S Tag, T7 tag, Strep tag, FLAG, chitin binding domain, and calmodulin binding protein.

6. The agent according to claim 1 which additionally specifically binds the sequence 5'-$^{Me}C^{Me}$CpGG-3', in vitro.

7. An agent which specifically binds 5'-$C^{Me}$CpGG-3' DNA sequences, in vitro, comprising recombinant full-length, active McrA protein (rMcrA) which protein is more than about 90% pure.

* * * * *